United States Patent [19]
Biedermann et al.

[11] Patent Number: 5,443,467
[45] Date of Patent: Aug. 22, 1995

[54] BONE SCREW

[75] Inventors: Lutz Biedermann, VS-Villingen; Jürgen Harms, Waldbronn-Reichenbach, both of Germany

[73] Assignee: Biedermann Motech GmbH, VS-Schwenningen, Germany

[21] Appl. No.: 198,949

[22] Filed: Feb. 18, 1994

[30] Foreign Application Priority Data

Mar. 10, 1993 [DE] Fed. Rep. Germany ...... 4307576.2

[51] Int. Cl.⁶ ............................................. A61F 5/04
[52] U.S. Cl. ............................... 606/65; 606/72; 606/54; 606/73
[58] Field of Search ........... 606/53, 60, 61, 65, 606/66, 72, 73, 86, 87, 103; 403/121, 83, 99, 101, 103, 121, 117

[56] References Cited

U.S. PATENT DOCUMENTS

| | | | |
|---|---|---|---|
| 4,299,212 | 11/1981 | Goudfrooy | 606/54 |
| 5,176,680 | 1/1993 | Vignaud et al. | 606/73 X |
| 5,190,543 | 3/1993 | Schläpfer | 606/72 X |
| 5,261,912 | 11/1993 | Frigg | 606/72 X |
| 5,306,275 | 4/1994 | Bryan | 606/65 X |

FOREIGN PATENT DOCUMENTS

| | | |
|---|---|---|
| 0443892A1 | 8/1991 | European Pat. Off. . |
| 0465158A2 | 1/1992 | European Pat. Off. . |
| 3923966A1 | 2/1991 | Germany . |
| 9202745.8 | 6/1992 | Germany . |
| WO01115 | 2/1991 | WIPO ................... 606/65 |

*Primary Examiner*—Peter A. Aschenbrenner
*Attorney, Agent, or Firm*—Donald Brown

[57] ABSTRACT

A bone screw comprises a receiver member (5) and a screw member (1) having a threaded portion (2) and a head (3) having a spherical segment-shaped portion. The receiver member (5) comprises an internal thread (10) for allowing a relative adjustment of receiver member and screw member and the connection of the receiver member with a round rod. A pressure means (12) acts onto the head (3) and the rod (16) is placed on top of the pressure means. The arrangement is locked by means of a rod locking nut (13) and a lock nut (14) is screwed onto an external thread (11).

7 Claims, 1 Drawing Sheet

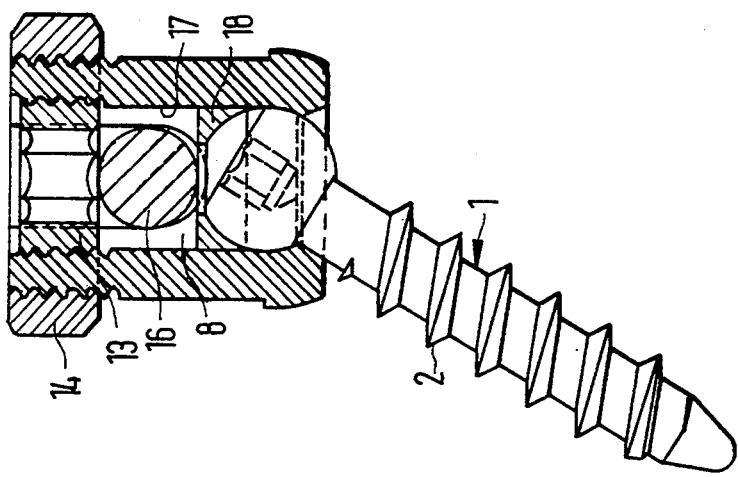
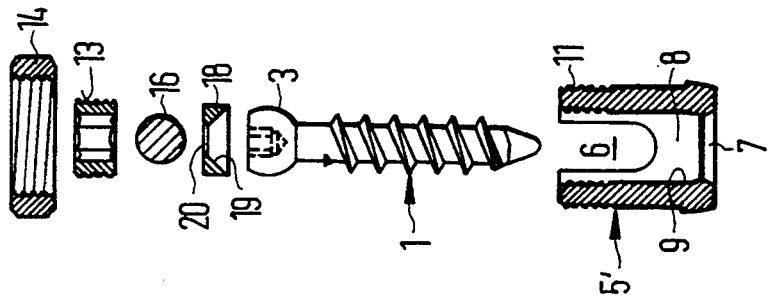
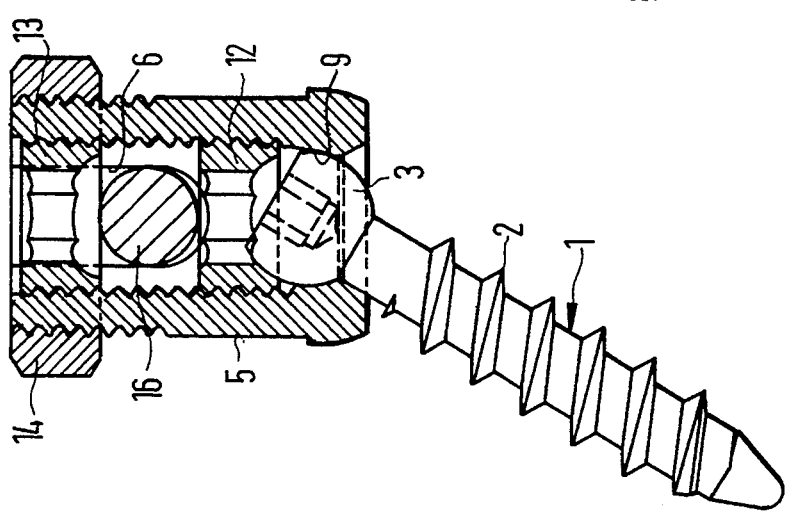
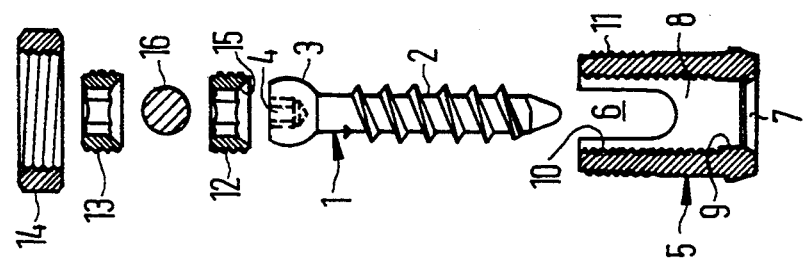

BONE SCREW

BACKGROUND OF THE INVENTION

The invention relates to a bone screw for connecting a bone with a rod.

A bone screw of this kind is disclosed in the German Patent Specification 39 23 966. This known bone screw comprises a screw member having a threaded portion and a head, said head having a spherical segment-shaped portion, a cylindrical receiver member for receiving the head of the screw member and the rod, the receiver member having a first end, a first bore provided at the first end for passing the threaded portion therethrough, a hollow spherical portion receiving the head at a position inwards adjacent to the bore, a second bore which is open towards the side opposite to the first bore for inserting a screw member and the head thereof. The rod to be connected to the bone screw is threaded and connected by means of two nuts provided on the threaded rod and engaging the exterior surface of the receiver member.

The European Patent Specification 0 465 158 discloses an anchoring member having a shaft to be anchored in the bone and a head for connection with a rod. The head has a substantially U-shaped cross-section with a base which is connected to the shaft and with two free legs forming a channel for receiving the rod. A first internal thread extends in direction of the legs at the inner side thereof, and a locking member as well as a further member embracing the outside of the legs are provided. The locking member and the embracing member are connected through an intermediate insert which is screwed into the internal thread of the two free legs. This known anchoring means requires that first the intermediate piece is locked with the embracing member and only thereafter the locking member is screwed in. The European Patent Specification 0 443 892 discloses an apparatus wherein an outer ring is placed around free legs of a head and the outer ring comprises a tongue engaging the channel. A locking member acting on the tongue when locked is screwed into an internal thread. A separate movement of the embracing member and of the locking member for manipulating the apparatus is not provided. A lock of the screws is also not provided and the fixation of a bent rod is not possible.

OBJECTS OF THE INVENTION

It is an object of the invention to provide an improved bone screw, in which the above-mentioned drawbacks are avoided. It is a further object of the invention to provide a bone screw of the above-mentioned kind which is adapted to be universally applicable in particular for treating corrections of the spinal column for fixing a round rod. It is a still further object to provide a bone screw which can be used in connection with a bent or curved rod.

SUMMARY OF THE INVENTION

According to the invention, a bone screw for connecting a bone with a rod comprises a screw member having a threaded portion and a head, said head having a spherical segment-shaped portion, a cylindrical receiver member for receiving said head of said screw member and said rod, said receiver member having a first end, a first bore provided at said first end for passing said threaded portion therethrough, a hollow spherical portion receiving said head at a position inwards adjacent to said bore, a second bore which is open towards the side opposite to the first bore for inserting said screw member and head thereof, said cylindrical receiver member further having a substantially U-shaped cross-section with two free legs which are provided with an external thread, and an internal thread, and a pressure means acting on said head, a locking screw screwed into said receiver member at said open end thereof for locking said rod when inserted into said U-shaped cross-section, and a lock nut screwed onto said external thread.

BRIEF DESCRIPTION OF THE DRAWINGS

Further advantages, features and objects of the invention will stand out from the following description of exemplary embodiments with reference to the drawings. In the drawings:

FIG. 1 shows a first embodiment of the invention in exploded and partly sectional representation;

FIG. 2 shows the screw of FIG. 1 in assembled state and on an enlarged scale;

FIG. 3 shows a further embodiment in exploded representation; and

FIG. 4 shows the screw of FIG. 3 in assembled state and on an enlarged scale.

DESCRIPTION OF PREFERRED EMBODIMENTS

The bone screw comprises the screw member proper 1 with a threaded portion 2 and a head 3. The head 3 has a spherical segment shape at the side adjacent to the threaded portion. A hole 4 for engagement with a hexagon socket screw key is provided at the head coaxially to the thread axis and at the end of the head opposite to the threaded portion 2.

The bone screw further comprises a cylindrical receiver member 5. The receiver member has a first axial bore 7 provided at one end thereof and having a diameter which is larger than the diameter of the threaded portion 2 and smaller than the diameter of the head 3. The receiver member 5 further comprises a coaxial second bore 8 which is open at the end of the receiver member opposite to the first bore 7 and has a diameter sized for passing the screw member through the open end, whereby the threaded portion is guided through the first bore 7 and the head 3 engages the base of the second bore. Between the first bore and the second bore there is a small coaxial section 9 which is immediately adjacent to the first bore and has a spherical surface towards the open end, whereby the radius of the spherical surface corresponds substantially to the radius of the spherical segment-shaped portion of the head 3. The second bore has an internal thread 10 which extends coaxially from the section 9 to the free end. The receiver member 5 further comprises a U-shaped recess 6 which is symmetric with respect to the center of the member and shaped so that the base thereof points towards the first bore 7 and the two lateral legs extend to the open end opposite to the first bore. An external thread 11 is provided at the free end of the legs of the U-shaped recess.

The screw member further comprises a head locking nut 12 and a rod locking nut 13 which both have an external thread corresponding to the internal thread 10. The head locking nut 12 has a spherical countersunk portion 15 at its side facing the head 3. Both locking nuts 12, 13 have respective hexagon socket surfaces for engagement with a hexagon socket screw key. Further, a lock nut 14 comprises an internal thread fitting onto the external thread 11.

In operation, the screw member 1 is passed through the open end of the second bore into the first bore. By engaging the hole 4 the screw member 1 is screwed into the spinal column. Thereafter, the head locking nut is first loosely screwed in towards the head 3 with a hexagon socket screw key. Thereupon, the receiver member 5 is correctly adjusted for receiving a round rod 16 to be connected with the bone screw. Having obtained this adjusted position, the head locking nut is tightened to such an extent that the screw member 1 is rigidly connected to the receiver member 5. Thereafter, the round rod 15 is finally inserted into the U-shaped recess 6 and positionally locked by inserting and tightening the rod locking nut 13. Thereafter, the lock nut 14 is screwed onto the free ends of the legs of the U-shaped recess 6 in the manner shown in FIG. 2. The rod locking nut 13 as well as the lock nut 14 are turned until they exert a desired fixing force onto the round rod 16. Thereby, the advantage is achieved that the force acting onto the rod 16 can be independently adjusted either by the rod locking nut 13 or by the lock nut 14. Moreover, a final fastening and screw retention by locking is obtained.

The separate fastening obtained by the rod locking nut 13 and by the lock nut 14 is in particular important when fastening curved rods rather than straight rods. In this case, an exact fastening is possible only by independent adjustment of both nuts.

As best shown in FIG. 2, the first bore 7 is conically shaped to taper such that the outer diameter is larger than the diameter at the side adjacent to the section 9. This allows the screw member 1 to pivot around an angle with respect to the axis of symmetry of the receiver member in the manner shown in FIG. 2.

In the following, the second embodiment shown in FIGS. 3 and 4 is described. The corresponding parts are identified by the identical reference signs.

The screw member 1, the rod locking nut 13 and the lock nut 14 correspond exactly to the first embodiment. Unlike in the above-described embodiment, a cyclindrical section 17 without internal thread is provided between the section 9 and the internal thread 10. A pressure disk 18 is provided in place of the head locking nut and formed to have a spherical countersunk portion 19 at its side facing the head 3. The radius of the countersunk portion 19 substantially corresponds to the radius of the spherical segment-shaped portion of the head 3. The outer diameter of the pressure disk 18 is selected so that the pressure disk 18 is slidable within the cylindrical section 17 and therefore displaceable towards the head within the cylindrical section 17. All other elements of the two embodiments are identical. Preferably, the pressure disk 18 has a coaxial bore 20 which provides access to the hole 4 and facilitates grasping the pressure disk 18.

In operation, the screw member, after insertion into the receiver member, is first screwed in as in the first embodiment. Thereafter, the pressure disk 18 and the rod 16 are inserted one after the other. Unlike the first embodiment, the screw member 1 and the receiver member 5 can be freely pivoted with respect to each other at this stage. Screw member 1 and receiver member 5 relative to each other and thus also rod 16 are fastened not before screwing in the rod locking nut 13. Thereafter, the lock nut 14 is again screwed on. Again, lock nut 14 and rod locking nut 13 are separately turned in direction to the base of the bore until each one of the two parts exerts a desired fastening force onto the rod 16.

With the two above-described embodiments, a connection is provided in one case wherein the screw member and the receiver member are rigidly connected and therefore adjusted with a fixed position relative to each other before fastening the rod 16, whereas in the second embodiment the final adjustment is not made before tightening the rod locking nut 13.

In a third embodiment, all parts correspond to the first embodiment. Additionally to or in place of the head locking nut 12, there is provided a pressure disk which corresponds to the pressure disk 18 and has an outer diameter selected so that the pressure disk can be slidably displaced along the internal thread towards the head 3 in the same sense as in the second embodiment. The fastening when using the pressure disk is thereafter obtained in the same manner as in the second embodiment.

It is the advantage of the third embodiment that store keeping is made easier because only one type of receiver member 5 is required which is suitable for both applications.

Although the invention has been described with reference to specific example embodiments, it is to be understood that it is intended to cover all modifications and equivalents within the scope of the appended claims.

What is claimed is:

1. A bone screw for connecting a bone with a rod, said bone screw comprising
   a screw member having a threaded portion and a head, said head having a spherical segment-shaped portion,
   a cylindrical receiver member for receiving said head of said screw member and said rod, said receiver member having a first end and a second end, a bore provided in said receiver member between said first and second ends, a hollow spherical portion in said bore for receiving said head at a position inwards of said second end, said cylindrical receiver member further having a substantially U-shaped cross-section with two free legs which are provided with an external thread, and an internal thread,
   a pressure means having a portion acting on said head, and
   a locking screw screwed onto said receiver member internal thread at said first end thereof for locking said rod in place when inserted into said U-shaped member cross-section and;
   a lock nut screwed onto said external thread.

2. A bone screw assembly for connecting a bone with a rod comprising
   a screw member having a head and a threaded portion, said head has a spherical segment shaped portion, a cylindrical receiver member with a substantially U-shaped cross-section with two free legs and having an axial bore with an internal threaded portion and a narrow portion means for maintaining the screw head in said bore while said screw threaded portion extends outside said bore,
   a first locking nut positioned on the internal threaded portion of the bore for engaging the head of said screw to hold it in place, and a second locking nut on said internal threaded portion of the bore for holding a rod positioned between said legs in place.

3. The bone screw of claim 2, wherein said receiver member has an external thread and wherein a third locking nut is positioned on the external thread.

4. The bone screw of claim 1, wherein said head has an engagement portion on its side opposite to said threaded portion for engagement with a screw driver.

5. The bone screw of claim 1, comprising a spherical segment-shaped portion formed on said pressure means at the side thereof facing said head, said spherical segment-shaped portion being directed to said head.

6. The bone screw of claim 1, wherein said pressure means is formed as a disk.

7. The bone screw of claim 1, wherein said pressure means is formed as a screw.

* * * * *